`US009683925B1`

United States Patent
Boyer et al.

(10) Patent No.: US 9,683,925 B1
(45) Date of Patent: Jun. 20, 2017

(54) TACTILE SENSOR SYSTEM AND METHOD FOR INSPECTING THE CONDITION OF A STRUCTURE

(71) Applicant: STATE FARM MUTUAL AUTOMOBILE INSURANCE COMPANY, Bloomington, IL (US)

(72) Inventors: Patrick H. Boyer, Bloomington, IL (US); Nathan L. Tofte, Downs, IL (US); Jackie O. Jordan, II, Bloomington, IL (US); Brian N. Harvey, Bloomington, IL (US)

(73) Assignee: STATE FARM MUTUAL AUTOMOBILE INSURANCE COMPANY, Bloomington, IL (US)

( * ) Notice: Subject to any disclaimer, the term of this patent is extended or adjusted under 35 U.S.C. 154(b) by 0 days.

(21) Appl. No.: 15/238,249

(22) Filed: Aug. 16, 2016

Related U.S. Application Data

(63) Continuation of application No. 15/009,269, filed on Jan. 28, 2016, now Pat. No. 9,442,061, which is a continuation of application No. 14/833,739, filed on Aug. 24, 2015, now Pat. No. 9,291,544.

(51) Int. Cl.
*G01N 19/08* (2006.01)
*G01N 27/00* (2006.01)
*E04B 7/00* (2006.01)

(52) U.S. Cl.
CPC ............... *G01N 19/08* (2013.01); *E04B 7/00* (2013.01); *G01N 27/00* (2013.01)

(58) Field of Classification Search
CPC ..................................... G01N 19/08
USPC .............................. 73/774; 348/47
See application file for complete search history.

(56) References Cited

U.S. PATENT DOCUMENTS

| 8,872,818 B2 | 10/2014 | Freeman et al. |
| 2014/0046589 A1 | 2/2014 | Metzler et al. |
| 2014/0267627 A1* | 9/2014 | Freeman ............... G01S 17/023 348/47 |

* cited by examiner

*Primary Examiner* — Lisa Caputo
*Assistant Examiner* — Jamel Williams
(74) *Attorney, Agent, or Firm* — Marshall, Gerstein & Borun LLP; Randall G. Rueth

(57) ABSTRACT

In a computer-implemented method and system for capturing the condition of a structure, the structure is scanned with a three-dimensional (3D) scanner. The 3D contact scanner includes a tactile sensor system having at least one tactile sensor for generating 3D data points based on tactile feedback resulting from physical contact with at least part of the structure. A 3D model is constructed from the 3D data and is then analyzed to determine the condition of the structure.

7 Claims, 7 Drawing Sheets

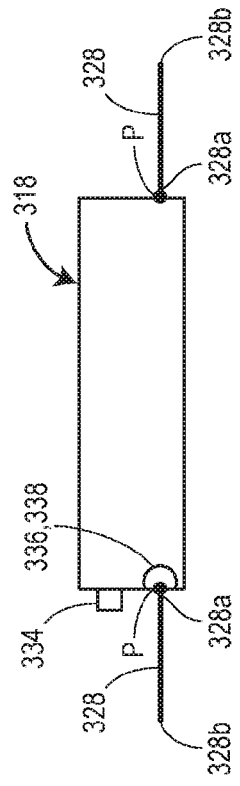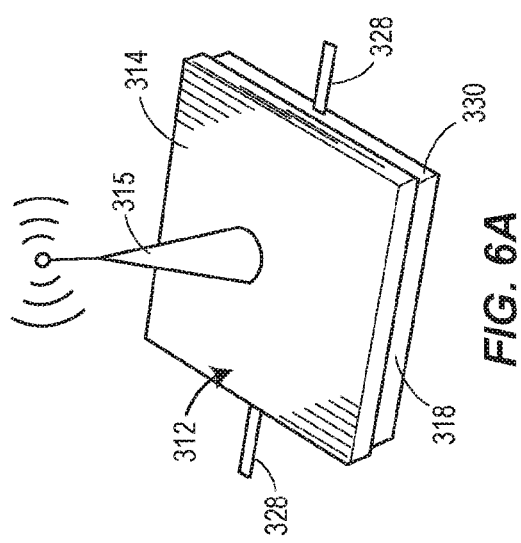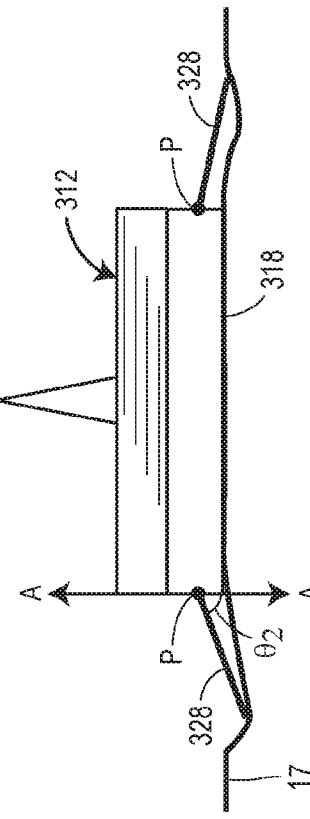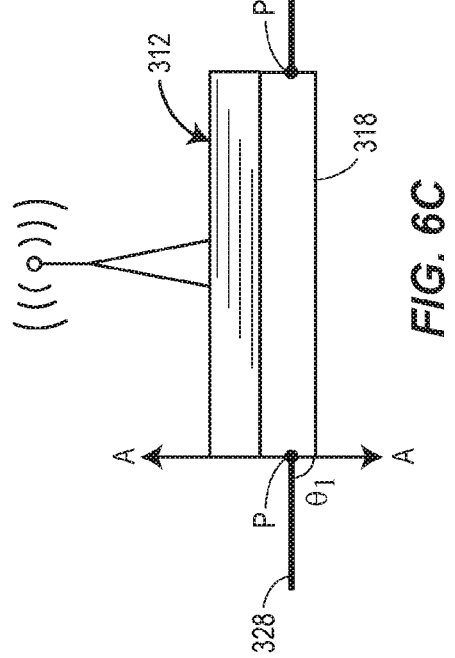
FIG. 6A
FIG. 6B
FIG. 6C
FIG. 6D

US 9,683,925 B1

TACTILE SENSOR SYSTEM AND METHOD FOR INSPECTING THE CONDITION OF A STRUCTURE

CROSS-REFERENCE TO RELATED APPLICATIONS

The present application is a continuation of U.S. application Ser. No. 15/009,269, filed Jan. 28, 2016, which is a continuation of U.S. application Ser. No. 14/833,739, filed Aug. 24, 2015, entitled "Tactile Sensor System and Method for Inspecting the Condition of a Structure," both of which are hereby incorporated by reference for all purposes.

TECHNICAL FIELD

This disclosure relates to property inspection methods and systems, and in particular, to property inspection system and method for capturing and/or estimating the condition of a structure using a tactile sensor system.

BACKGROUND

The present disclosure generally relates to a system or method for inspecting a structure to estimate the condition of the structure. After an accident or loss, property owners typically file claims with their insurance companies. In response to these claims, the insurance companies assign an appraiser to investigate the claims to determine the extent of damage and/or loss, document the damage, and provide its clients with appropriate compensation.

Determining and documenting the extent of damage can be risky for the appraiser. For example, in a situation where a structure has experienced roof damage, appraisers typically climb onto the roof to evaluate the damage. Once on the roof they may sketch the damaged area of the roof to document the damage. Alternatively, appraisers might take a digital picture of the damaged area. In either scenario, the appraiser has exposed himself to a risk of falling. Afterwards, the picture is typically attached to an electronic claim file for future reference where it can be analyzed by an appraiser to estimate the extent of damage to the structure.

The process for determining and documenting the extent of the damage can be inefficient and time consuming. In addition to the time required to drive to and from the incident site and to perform the inspection itself, significant paperwork and calculations may be involved in calculating compensation owed to the clients. For example, after taking pictures of a roof, the appraiser may have to come back to his office, research the client's property, research the cost of the damaged property and research repair costs to calculate how much money a client should be paid. All of these steps are time consuming and both delay payment to the client and prevent the appraiser from assessing other client claims.

In situations where the insurance company has received a large number of claims in a short time period (e.g., when a town is affected by a hurricane, tornado, or other natural disaster), an insurance appraiser may not have time to perform a timely claim investigation of all the received claims. If claim investigations are not performed quickly, property owners may not receive recovery for their losses for long periods of time. Additionally, long time delays when performing claim investigations can lead to inaccurate investigations results (e.g., the delay may lead to increased opportunity for fraud and/or may make it more difficult to ascertain the extent of damage at the time of the accident or loss).

Further, two-dimensional digital pictures or video of a roof or structure often provide inadequate detail for thorough inspection of a structure. Poor image quality resulting from camera movement or out-of-focus images can make it difficult to estimate the condition of a property based on an image. Even where image quality is adequate, poor angles or bad lighting may hide or exaggerate details important to estimating the condition of the structure, leading to inaccurate assessments of the structure's condition. In addition, two-dimensional pictures or video also fail to provide any detail about a subsurface of the roof or structure.

Still further, three-dimensional imaging of a roof or structure, such as laser scanning and ultrasonic scanning, also often provides inadequate detail for a thorough inspection of a structure. While three-dimensional imaging can provide some detail about a subsurface of a roof, for example, three-dimensional imaging is often compromised and inaccurate due to interfering sunlight during the scan on the roof or other structure. In addition, ultrasonic scanning typically requires a jelly-like sound conductor for an adequate scan and problems with proper application and removal of the jelly-like substance make three-dimensional ultrasonic scanning more time consuming, messy, and costly.

SUMMARY

A system and method of inspecting the condition of a structure is disclosed. In one example, the method of inspecting a structure comprises deploying one or more three-dimensional (3D) contact scanners to scan a structure, wherein the one or more 3D contact scanners are communicatively connected to a memory. The method further comprise detecting 3D information by implementing a tactile sensor system of the one or more 3D contact scanners across a surface of at least part of the structure. The tactile sensor system includes at least one tactile sensor, and the at least one tactile sensor includes one or more of a pinscreen stamp having a plurality of pins, a roller device having a plurality of disks, or a whisker device having one or more of at least one whisker and a piezoelectric sensor. Implementing the tactile sensor system includes one or more of moving, rolling or dragging the at least one tactile sensor on a physical surface of at least part of the structure; and measuring one or more of: (1) resistance to pressure being applied to at least one point of a plurality of points on the surface of at least part of the structure via the at least one tactile sensor; or (2) a depth of at least one point of the plurality of points on the surface of the at least part of the structure via at least one tactile sensor.

The method further comprises generating, at the one or more 3D contact scanners, a plurality of 3D data points, wherein at least one point of the plurality of 3D data points corresponds to at least one point of the plurality of points on the surface of the structure detected by the at least one tactile sensor. The method further comprises causing a processor communicatively connected to the memory to generate an estimation of the condition of the structure based on the plurality of data points.

In another example of the present disclosure, a property inspection system for determining the condition of a physical structure comprises one or more 3D contact scanners adapted to scan a surface of the structure and at least one tactile sensor system coupled to the one or more 3D contact scanners. The tactile sensor system may include at least one tactile sensor having one or more of a pinscreen stamp, a roller device having a plurality of disks, or a whisker device having one or more of at least one whisker and a piezoelectric sensor. The at least one tactile sensor is adapted to detect 3D information about the surface of the structure by: (1) one or more of moving, rolling, and/or dragging the at least one sensor of the tactile sensor system on a physical surface of the structure; and (2) measuring one or more of: (a) resistance to pressure being applied to at least one point of a plurality of points on the surface of the structure; or (b) a depth of the at least one point of the plurality of points on the surface of the structure. The system further includes one or more processors for generating 3D data points corresponding to the 3D information detected by the tactile sensor system, and a memory communicatively coupled to the one or more 3D contact scanners. The memory may store the 3D data points generated by the one or more processors and the 3D information detected by the at least one tactile sensor. The system further includes a network interface, communicatively coupled to the one or more processors, for transmitting the 3D data points to a data analysis system for estimating the condition of the structure.

BRIEF DESCRIPTION OF THE DRAWINGS

FIG. 6A is a perspective view of a 3D contact scanner and a tactile sensor system according to another aspect of the property inspection system of the present disclosure;

FIG. 6B is a bottom perspective view of the tactile sensor system of FIG. 6A;

FIG. 6C is a side perspective view of the tactile sensor system of FIG. 6A;

FIG. 6D is a side perspective view of the tactile sensor system of FIG. 6A in contact with the surface of the structure.

DETAILED DESCRIPTION

Generally, a property inspection system and method for determining the condition of a physical structure is disclosed. The property inspection system includes one or more three-dimensional (3D) contact scanners adapted to scan a surface of the structure, and at least one tactile sensor system coupled to the one or more 3D contact scanners. The tactile sensor system includes at least one tactile sensor comprising one or more of a pinscreen stamp, a roller device having a plurality of discs, and a whisker device having one or more of at least one whisker and a piezoelectric sensor. The at least one tactile sensor is adapted to detect 3D information about the surface of the structure by: (1) one or more of moving, rolling and/or dragging the at least one sensor of the tactile sensor system on a physical surface of the structure; and (2) measuring one or more of: (a) resistance to pressure being applied to at least one point of a plurality of points on the surface of the structure; or (b) a depth of the at least one point of the plurality of points on the surface of the structure.

Figure 1:
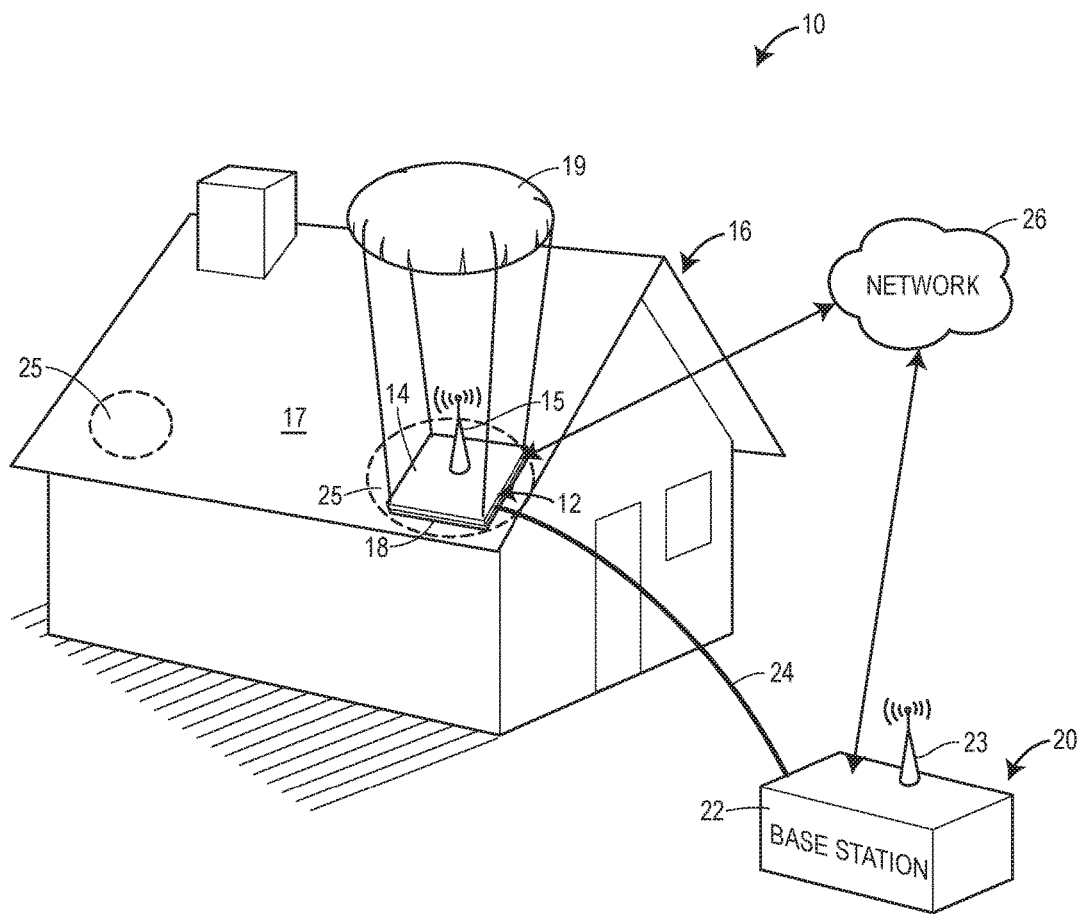
FIG. 1 is a perspective view of a property inspection system according to one example of the present disclosure.

Referring now to FIG. 1, a property inspection system 10 of the present disclosure is depicted. The property inspection system 10 includes at least one 3D contact scanner 12 having a base 14, an antenna 15, and at least one tactile sensor system 18 coupled to the base 14 of the 3D contact scanner 12. The 3D contact scanner 12 is disposed on a structure 16, in particular a surface 17 of the structure 16, such as a roof, to determine the condition of the physical structure 16, for example. In one example, the 3D contact scanner 12 may be held and operated by a person. In another example, the 3D contact scanner 12 is affixed to a flying device 19, which may be used to position the 3D contact scanner 12 onto the surface 17 of the structure 16, e.g., the roof of the structure 16. While the flying device 19 depicted in FIG. 1 is a balloon, the flying device 19 may alternatively be an airplane, a helicopter, a projectile, a rocket, or any other device capable of flight, levitation or gliding, and may be tethered via a tether line 24 to a base station 22 of a data analysis system 20. In some examples, the tether 24 may provide power to the flying device 19. The tether 24 may also provide a communication channel between the flying device 19 and the base station 20 (and may replace the antennas 15, 23 in certain examples). In yet another example, the 3D contact scanner 12 may also be affixed to a remotely controlled device, such as a radio controlled device; a device that rolls, drives, crawls, climbs or drives; a mechanical apparatus affixed to or near the structure; or a satellite.

The property inspection system 10 may further include a data analysis system 20 for estimating the condition of the structure 16. The data analysis system 20 may include a base station 22 and antenna 23, which may be in communication with the antenna 15 of the 3D contact scanner 12, as explained more below. Alternatively, the data analysis system 20 of the property inspection system may be in communication with the 3D contact scanner 12 via a network 26, such as a wireless network. The network 26 may be a single network, or may include multiple networks of one or more types (e.g., a public switched telephone network (PSTN), a cellular telephone network, a wireless local area network (WLAN), the Internet, etc.). In some examples, the network 26 may include one or more devices such as computers, servers, routers, modems, switches, hubs, or any other networking equipment.

While the structure 16 depicted in FIG. 1 is a building, which may be residential, commercial, industrial, agricultural, educational, or of any other nature, the structure 16 may be any type of construction or object and still fall with the scope of the present disclosure. For example, the structure 16 may alternatively be personal property, such as a vehicle, boat, aircraft, or furniture.

The property inspection system 10 may be utilized in a number of situations, but in the preferred embodiment, a user associated with an insurance company utilizes the property inspection system 10 for the purpose of estimating the condition of the structure 16. In one example, an insurance policy-holder may file a claim because the policy-holder believes that the structure 16 is damaged. A user (e.g., an insurance company or claim adjuster) may then deploy the property inspection system 10 to inspect the structure 16 and estimate the condition of the structure 16. For example, the property inspection system 10 may determine that the roof of the structure 16 is damaged and then calculate how much it will cost to fix the roof. With regard to a vehicle, boat, or aircraft, the property inspection system 106 may determine that a body panel, window, frame, or another surface associated with the vehicle, boat, or aircraft is damaged. The property inspection system 10 may calculate a cost to fix the body panel, window, frame, or other surface. In other examples, the user may be an appraiser appraising the structure 16 or an inspector inspecting the structure 16.

Figure 2:
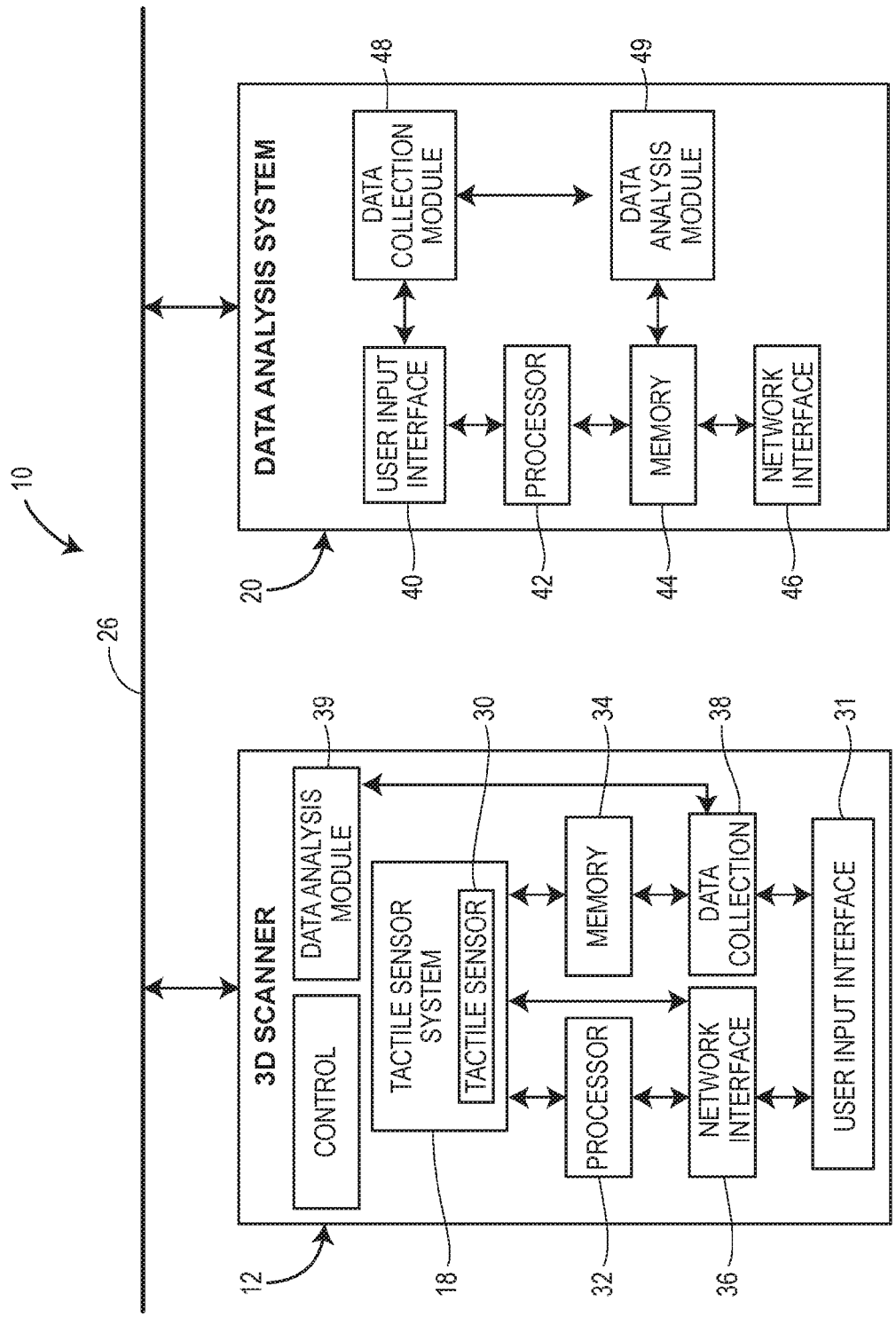
FIG. 2 is a block diagram of the property inspection system of FIG. 1.

Referring now to FIG. 2, a block diagram of the property inspection system 10 of FIG. 1 is depicted. More specifically, the property inspection system 10 includes the 3D contact scanner 12 that is communicably coupled to the data analysis system 20 via the network 26. Alternatively, the 3D contact scanner 12 may be coupled to the data analysis system 20 via a direct wired connection. The 3D contact scanner includes the tactile sensor system 18 that includes at least one tactile sensor 30, a processor 32, a memory 34 and a network interface 36. In certain examples, the tactile sensor 30 is controlled by the 3D contact scanner 12, as explained more below. The data analysis system 20 also includes a user input interface 40, at least one processor 42, a memory 44, and a network interface 46.

In certain examples, the memory 34 of the 3D contact scanner system and the memory 44 of the data analysis system 20 may include volatile and/or non-volatile memory and may be removable or non-removable memory. For example, the memory 34, 44 may include computer storage media in the form of random access memory (RAM), read only memory (ROM), EEPROM, FLASH memory or other memory technology, CD-ROM, digital versatile disks (DVD) or other optical disk storage, magnetic cassettes, magnetic tape, magnetic disk storage or other magnetic storage devices, or any other medium which can be used to store the desired information. In addition, the network interface 36, 46 may include an antenna, a port for wired connection, or both.

As further depicted in FIG. 2, each of the 3D contact scanner 12 and the data analysis system 20 may also include a data collection module 38, 48 and a data analysis module 39, 49, respectively. In the property inspection system 10, the data collection modules 38, 48 and the data analysis modules 39, 49 may be in direct wired or wireless communication with each other. Furthermore, in other examples, the data collection modules 38, 48 and the data analysis module 39, 49 may exist on a single device or platform and may share components, hardware, equipment, or any other resources.

In operation of one example of the property inspection system 10, the data collection module 38 generates data representing information detected by the tactile sensor system 18. The data collection module 38 transmits the generated data over the network 26. The data analysis module 49 receives the generated data from the network 26, where the data analysis module 49 operates to estimate the condition of the structure by analyzing the generated data. In some embodiments, estimating the condition of the structure may include comparing the generated data to reference data. The reference data may be any type of data that can provide a point of comparison for estimating the condition of the structure. For example, the reference data may represent an image, model, or any previously collected or generated data relating to the same or a similar structure. The reference data may also represent stock images or models unrelated to the scanned structure, that are stored, for example, in the memory 44 of the data analysis system 20. Furthermore, the data analysis module 49 may use the estimate of the condition of the structure to determine that the structure is damaged, and then may calculate an estimated cost correlated to the extent of the damage to the structure.

In some embodiments of the property inspection system 10, the data collection module 38 of the 3D contact scanner 12 wirelessly transmits, and the data analysis module 49 of the data analysis system 20 wirelessly receives, the generated data. In one example, the generated data corresponds to tactile characteristics of the scanned structure, as explained more below.

In operation of the 3D contact scanner 12, the network interface 36 receives data representing a command to collect 3D information associated with the structure 16 (e.g., a "3D capture command"). The network interface 36 transmits the 3D capture command to the processor 32, where the 3D capture command data is received. The processor 32 then transmits a signal instructing the 3D contact scanner 12 to detect 3D characteristics associated with an object. The 3D contact scanner 12 scans, such as detects, the structure 16 and generates data representing 3D characteristics of the structure 16 ("3D data") corresponding to the collected 3D information.

Figure 3:
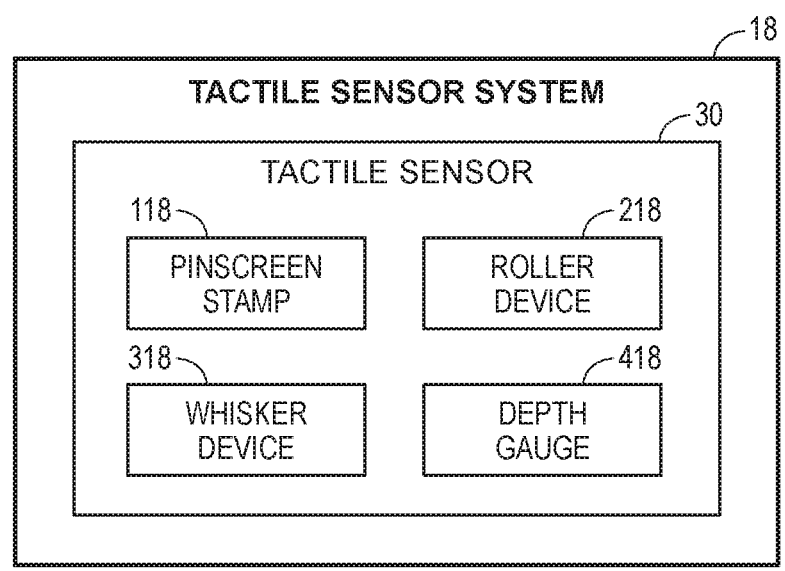
FIG. 3 is a block diagram of a tactile sensor system of FIGS. 1 and 2.

Referring now to FIG. 3, the tactile sensor 30 of the tactile sensor system 18 of FIG. 2 may include one or more sensing mechanisms, e.g., tactile sensors, including a pinscreen stamp 118, a roller device 218, a whisker device 318, or a depth gauge 418, each of which are explained in more detail below. As one of ordinary skill in the art will appreciate, the tactile sensor system 18 may have at least one tactile sensor 30, any combination of the tactile sensors 30, or all of the tactile sensors 30. In one example, the tactile sensor 30 may include only the pinscreen stamp 118. In another example, the tactile sensor may include only the roller device 218, and in yet other examples, the tactile sensor 30 may include only the whisker device 318 or only the depth gauge 418. In still other example, the at least one tactile sensor 30 includes the pinscreen stamp 118 and the roller device 218. In another example, the at least one tactile sensor includes the pinscreen stamp 118 and the whisker device 318. In another example, the at least one tactile sensor 30 includes the roller device 218 and the whisker device 318. In another example, the at least one tactile sensor 30 includes the pinscreen stamp 118 and the depth gauge 418 or the roller device 218 and the depth gauge 418. In yet another example, the at least one tactile sensor 30 includes the pinscreen stamp 118, the roller device 218, the whisker device 318 and the depth gauge 418.

Figure 4B:
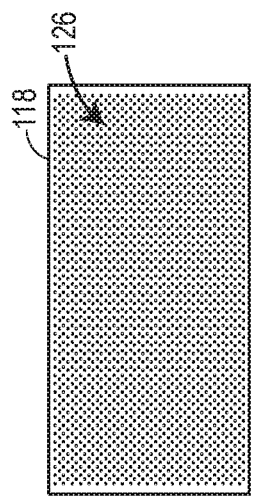
FIG. 4B is a bottom view of the tactile sensor system of FIG. 4A.
Figure 4C:
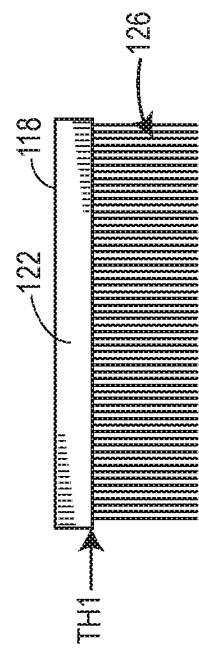
FIG. 4C is a side perspective view of the tactile sensor system of FIG. 4B.
Figure 4D:
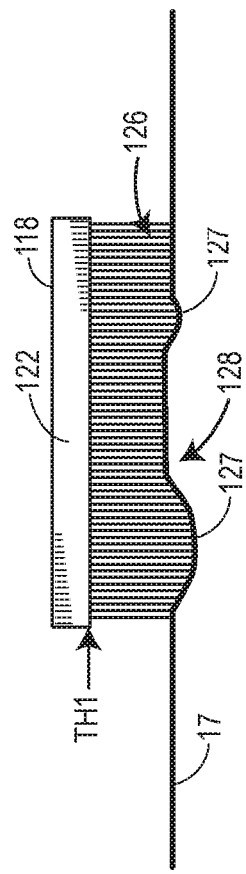
FIG. 4D is another side perspective view of the tactile sensor system of FIG. 4B in contact with and having pressure being applied toward a surface of the structure.
Figure 4A:
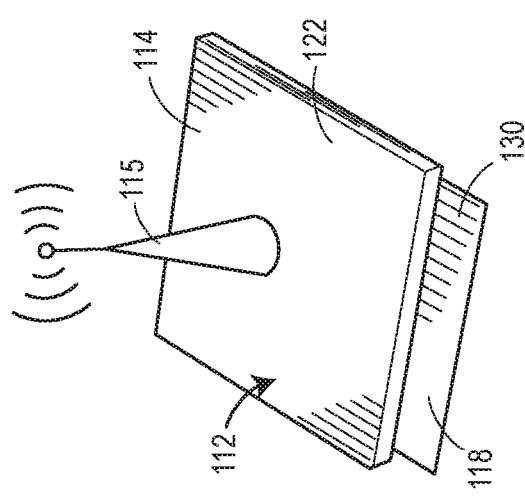
FIG. 4A is a perspective view of a 3D contact scanner and a tactile sensor system according to one aspect of the property inspection system of the present disclosure.

Referring now to FIGS. 4A-4D, a 3D contact scanner 112 having a base 114 and a tactile sensor system 118 coupled to the base 114 is depicted, the tactile sensor system 118 having at least one tactile sensor 130. In this example, the tactile sensor system 118 is a pinscreen stamp 118 having a plurality of pins 126. More specifically, the pinscreen stamp 118 includes a top portion 122 that includes a plurality of pins 126 extending therefrom. When no pressure is applied at or from the top portion 122 in a direction toward the plurality of pins 126 extending therefrom, the length of each pin of the plurality of pins 126 is approximately the same, if not equal, in one example, as depicted in FIG. 4c. However, when pressure is applied to the top surface 122 of the pinscreen stamp 118 in a direction of the surface 17 of a structure 16, e.g., a roof, and such that the pins of the plurality of pins 126 are in contact with the surface 17 (FIG. 4d), several pins of the plurality of pins will move to match the surface 17. In other words, any cracks, holes, divots, and/or markings 127 on the surface 17 will be identified because the pins of the plurality of pins 126 will move and/or adjust to the height of any of the cracks, divots, or markings on the surface, such that an imprint 128 is formed by the plurality of pins 126 of the pinscreen stamp 118.

Said another way, a depth of at least one point of a plurality of points 25 (FIG. 1) on the surface 17 of at least part of the structure 16 may be measured by stamping or pushing the pinscreen stamp 118 onto the surface 17 of at least part of the structure 16 after the 3D contact scanner 12 is moved to the physical surface 17 of the structure 16. When this occurs, the plurality of pins 126 form an imprint 128 of the plurality of points 25 on the surface 17 of the structure 16. As such, the change in height of at least one pin of the plurality of pins 126 measured from a first threshold TH1 (FIGS. 4C and 4D) of the pinscreen stamp 118 when no pressure is applied from when pressure is applied to the pinscreen stamp 118 corresponds to a depth of at least one point of the plurality of points 25 of the surface 17. In another example, stamping and pushing the pinscreen stamp 118 comprises pushing at least one pin of the plurality of pins 126 into at least one point of the plurality of points 25 on the surface 17 of the structure 16 and transmitting the imprint 128 corresponding to the plurality of points 25 to the processor 32 of the 3D contact scanner 12. As a result, the processor 32 identifies a plurality of positions of the plurality of pins 126 and transmits the information to the data analysis system 20. The data analysis system 20 then generates a 3D model or map of the surface 17 of the structure 16 based on the positions of the plurality of pins 126, for example. In another example, the processor 32 of the 3D contact scanner 12 generates the 3D model or map of the surface 17 of the structure 16 based on the positions of the plurality of pins 126.

More generally, and as one of ordinary skill in the art will appreciate, the 3D contact scanner 112 of the present disclosure may measure resistance to pressure being applied to one or more points of the plurality of points 25 (FIG. 1) via a pin of the plurality of pins of the pinscreen stamp 118 or a pin or rod actuator (not shown) of the tactile sensory system 18 to determine the condition of the structure 16. More specifically, resistance to pressure being applied to the plurality of points 25 may be measured by first applying pressure to at least one point of the plurality of points 25 via at least one tactile sensor 130. The tactile sensor 130 may include one or more of the pinscreen stamp 118, a pin of the plurality of pins, or rod of an actuator (not shown) attached to the 3D contact scanner 112. Resistance to the pressure being applied is measured by the pinscreen stamp 118 or pin and transmitted to the memory 34 of the 3D contact scanner 112, for example. The measured resistance of at least one point of the plurality of points 25 is then compared, via the processor 32 of the 3D contact scanner, for example, to a measured resistance for another point of the plurality of points. The comparison helps determine if there is any indication of loss of strength or lack of strength for at least one point of the plurality of points 25 on the surface 17 of the structure 18.

In one example, a first pressure is applied to at least one point of the plurality of points 25 via the at least one tactile sensor 30 and the resistance to the pressure applied is measured as a first resistance. Then a second pressure, e.g., a pressure greater than the first pressure applied, is applied to the at least one point of the plurality of points 25 via the at least one tactile sensor 30 and the resistance to the second pressure is measured as a second resistance. A comparison, via one or more processors, e.g., processor 32, of the difference in the first resistance measured for the at least one point of the plurality of points to the second resistance measured for the at least another point of the plurality of points is made. This comparison helps determine if there is any indication of a lack of strength for at least one point of the plurality of points on the surface of the structure. Still further, the measured first resistance to the first pressure applied to at least one point of the plurality of points 25 and the measured second resistance to the second pressure applied to at least one point of the plurality of points 25 may be compared to a threshold resistance of the at least one point of the plurality of points of the undamaged area 25 (FIG. 1) on the surface 17 of the structure 16.

In addition, measuring resistance to pressure being applied to the plurality of points 25 may further comprise first calibrating the at least one tactile sensor 130. Calibration includes first applying pressure to another plurality of points 25 on a known, undamaged area of on the surface 17 of the structure 16. For example, the 3D contact scanner 112 first measures a resistance to pressure being applied to at least one point of the second plurality of points 25 (FIG. 1) and sets the measured resistance as a threshold resistance TR. The measured resistance to the pressure applied to at least one point of the plurality of points 25 via the at least one tactile sensor 30 of the tactile sensor system 18 is then compared to the threshold resistance TR of the at least one point of the plurality of points 25 of the undamaged area on the surface 17 of the structure 16. The comparison helps determine if there is any indication of loss of strength or lack strength on the surface of the structure 16.

Figure 5A:
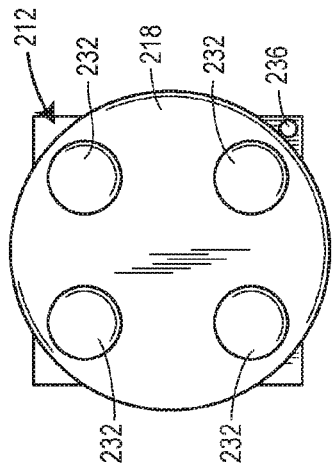
FIG. 5A is a perspective view of a 3D contact scanner and a tactile sensor system according to another aspect of the property inspection system of the present disclosure.
Figure 5B:
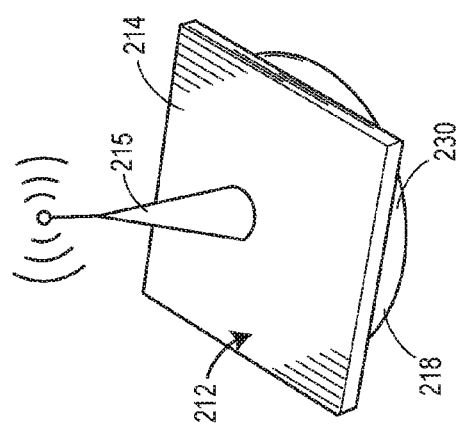
FIG. 5B is a bottom perspective view of the tactile sensor system of FIG. 5A.

Referring now to FIGS. 5A-5D, another 3D contact scanner 212 according to the property inspection system 10 of the present disclosure is depicted. Like the 3D contact scanner 112 of FIG. 4A, for example, the 3D contact scanner 212 includes a base 214 and an antenna 215 removably attached to a top surface of the base 214. In this example, a tactile sensor system 218 is a roller device 218 that includes at least one tactile sensor 230 and is attached to a bottom surface of the base 214 of the 3D contact scanner 212. As depicted in FIG. 5B, a bottom surface of the roller device 218 includes a plurality of disks, such as four disks 232 that are equally spaced along a circumference of the roller device 218. While four disks 232 are depicted in FIG. 5B, one of skill in the art will appreciate that fewer or more disks 232 may alternatively be included on the roller device 218 and not depart from the scope of the present disclosure.

Figure 5C:
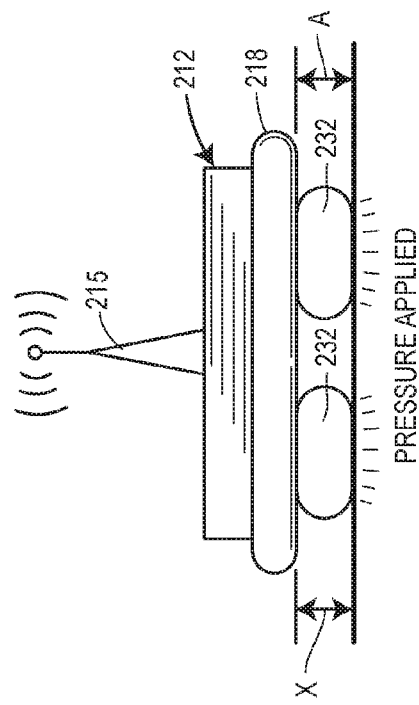
FIG. 5C is a side perspective view of the tactile sensor system of FIG. 5A with no pressure being applied toward a surface of a structure.

In operation, the 3D contact scanner 212 having the roller device 218 is first moved onto and then rolled across and/or about the physical surface 17 of at least part of the structure 16 (FIG. 1). Generally, while being rolled across and/or about the surface 17, the roller device 218 applies pressure to the plurality of disks 232 toward the direction of the surface 17 of the structure 16 and then measures resistance to the pressure being applied to the plurality of points 25 on the surface 17. In one example, the roller device 218 measures pressure being applied to the plurality of points 25 by first applying a zero pressure to at least one disk 232 of the plurality of disks of the roller device 218. The height of at the at least one disk 232 when zero pressure is being applied is then measured, which may be a threshold height TH2, as depicted in FIG. 5C.

After the roller device 218 is calibrated, e.g., a threshold height is measured, a first pressure P1 is applied to at least one disk 232 of the roller device 218 toward the direction of the surface 17. The height of the at least one disk 232 with the first pressure P1 being applied is then measured. For example, the height of at least one disk 232 in FIG. 5D after the first pressure has been applied is measured as X. The height X of the at least one disk 232 after the first pressure P1 has been applied is then compared against the threshold height TH2 of the at least one disk 232 when no pressure is applied. The comparison helps determine if there is an indication of sponginess or a lack of strength in a point of the plurality of points 25 in the surface 17 of the structure, e.g., a shingle. More specifically, the measured height X of the at least one disk 232 when a first pressure P1 is applied may be subtracted from the threshold pressure TH2 when zero pressure is applied to the at least one disk 232 to determine the difference in height Y when the two different pressures are applied. Said another way, the difference in height of at least one disk 232 when no pressure is applied and when the first pressure is applied is TH2−X=Y, with TH2 being the measured height when zero pressure is applied and X being the measured height when another pressure, such as the first pressure P1, is applied. This difference in height Y ultimately helps determine whether there is a lack of strength at a particular point of the plurality of points on the surface 17 of the structure 16.

Figure 5D:
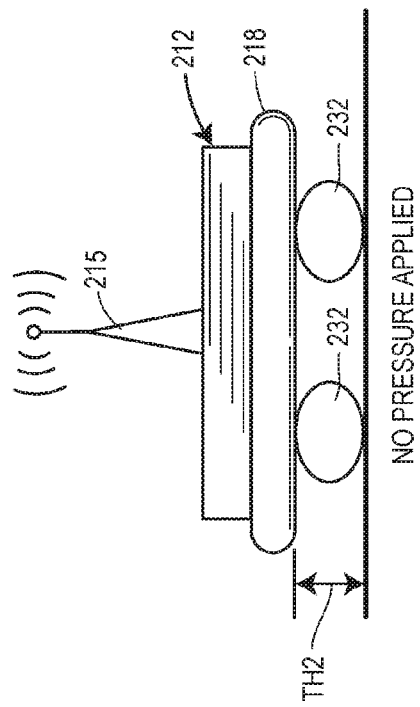
FIG. 5D is another side perspective view of the tactile sensor system of FIG. 5A with pressure being applied toward the surface of the structure.

In addition, the measured height of at least one disk 232 of the plurality of disks may be different from the measured height of another disk 232 when the same amount of pressure is applied. For example, and as depicted in FIG. 5D, when the first pressure P1 is applied to the disks 232 of the plurality of disks, the height of the leftmost disk 232 of the plurality of disks is one value, such as X, while the height of the rightmost disk 232 is a different value, such as A. This is because the point or points of the plurality of points 25 on which the plurality of disks of the roller device 218 are being applied are different for each disk 232 of the plurality of disks. As a result, there may be more weakness in the surface 17 at one point of the plurality of points 25 than another point of the plurality of points 25, such that the heights of the disks 232 differ for at least one point of the plurality of points while the same pressure is being applied. As such, in this example, the measured height A of the rightmost disk 232 depicted in FIG. 5A is compared against and/or subtracted from the measured height TH2 of the same disk 232 when zero pressure is applied to determine the difference in height B. This difference in height B also helps determine if there is a lack of strength and/or weakness at a particular point or at least one point of the plurality of points on the surface 17 of the structure 16.

While FIG. 5D and the foregoing example explains that a first pressure P1 is applied, one of ordinary skill in the art will understand that further increased pressures may be applied to the at least one disk 232 of the plurality of disks to further determine decreased strength and/or sponginess of the surface 17 of the structure 16. For example, a second increased pressure P2 may be applied to at least one disk 232 of the plurality of disks and the height of the at least one disk 232 may be measured when the second pressure P2 is applied. The measured heights of the at least one disk 232 when zero pressure is applied and when the first pressure P1 is applied may then be compared to the measured height of the at least one disk 232 when the second pressure P2 is applied to determine if there is a lack of strength or sponginess of a point of the plurality of points 25 on the surface 17 of the structure 16.

Referring back to FIG. 5B, in some examples, a camera 236 may be disposed on a bottom side of the base 214 of the 3D contact scanner 212, adjacent to the roller device 218. During operation of the roller device 218, the camera 236 records the movement, such as vertical movement and/or up and down movement of at least one disk 232 of the plurality of disks. The vertical movement or up and down movement is then measured and is indicative of discrete depths of the surface 17, e.g., shingle, of the structure 16 at the plurality of points 25, for example. Said another way, the depth of at least one point of the plurality of points 25 (FIG. 1) on the surface 17 of the structure is measured after the camera 236 records the vertical movement of at least one disk 232 of the plurality of disks as the roller device 218 is rolling across and/or being dragged across the surface 17 of the structure 16. While the camera 236 is depicted on the 3D contact scanner 212 of FIG. 5B, one of ordinary skill in the art will appreciate and understand that the camera 236 may be disposed on any of the 3D contact scanners 12, 112, 212, 312 of the present disclosure and used with any of the tactile sensors 30, 130, 230, 330 of the present disclosure and still fall with the scope of the present disclosure.

Referring now to FIGS. 6A-6D, another 3D contact scanner 312 according to the property inspection system 10 of the present disclosure is depicted. Like the 3D contact scanner 212 of FIG. 4A, for example, the 3D contact scanner 312 includes a base 314 and an antenna 315 removably attached to a top surface of the base 314. In this example, a tactile sensor system 318 is attached to a bottom surface of the base 314 of the 3D contact scanner 312 and includes at least one tactile sensor 330 that is a whisker device 318. In one example, the whisker device 318 includes at least one whisker 328 having a first end 328*a* that is attached to a portion of the whisker device 318, forming a pivot point P. The whisker 328 also includes a second end 328*b* disposed opposite the first end 328*a* that is adapted to contact the surface 17 of the structure 16 while the whisker device 318 and 3D contact scanner 212 are being dragged across the surface 17. The whisker device 318 further includes one or more of a potentiometer 336 or an optical encoder 338 disposed on or coupled to the whisker device 318.

In operation, the depth of at least one point of the plurality of points 25 on the surface 17 of the structure 16 is measured by detecting a whisker angle of at least one whisker 328 at at least one point of the plurality of points 25. The depth of at least one point of the plurality of points 25 on the surface 17 of the structure 16 is then measured based on the detected whisker angle. More specifically, and for example, the whisker angle θ of the at least one whisker 328 is detected by measuring one or more of an angle of deflection or an angle of rotation of the at least one whisker 328 of the whisker device 318 from an axis A (FIG. 6C) of the pivot point P of the at least one whisker 328 of the whisker device 318 by one or more of the potentiometer 336 or the optical encoder 338. In one example, and referring to FIG. 6C, the whisker angle θ of the whisker 328 is $\theta_1$ when the whisker device 318 is not being dragged across the surface 17 of the structure and/or in a position that is not in contact with any surface of any structure. As further depicted in FIG. 6D, however, when the 3D contact scanner 312 with the whisker device 318 is moved to the surface 17 of the structure 16 and then dragged across or along at least one point of the plurality of points 25 of the surface 17 of the structure 16, the whisker angle θ, such as an angle of rotation or an angle of deflection of the at least one whisker 328, may decrease to θ₂ as the whisker 328 moves down and into a divot, marking, or damaged area of the surface 17 of the structure 16 to measure the depth of a point of the plurality of points 25.

In yet another example, the whisker device 318 of FIGS. 6A-6D may alternatively and/or additionally include a piezoelectric sensor 334 (FIG. 6B). The piezoelectric sensor 334 generates and measures voltage, if any, on at least one point of the plurality of points 25 on the surface 17 of the structure 16. The depth of the at least one point of the plurality of points 25 is then determined based on the voltage generated by the piezoelectric sensor 334.

In one example, the whisker 328 of the whisker device 318 is a wire, such as a metal wire or a plastic wire, and in another example the whisker 328 is a flange, such as a metal flange or a plastic flange. More specifically, the whisker 328 may include plastic material, such as polyurethane or any other similar plastic or combination of plastics that is able to deflect in response to changes in depth of the surface 17 of the structure 16, for example. One of ordinary skill in the art will further understand that the whisker 328 may comprise any other material similar to the deflective metal or plastic-based wire or flange and not depart from the scope of the present disclosure.

In yet another example, the tactile sensor system 18 of the 3D contact scanner 12 may further include a depth gauge 418, as depicted in FIG. 3. When the 3D contact scanner 12 is moved to the plurality of points 25 on the surface 17 of the structure 16, the 3D contact scanner 12 is then disposed on the plurality of points 25 of the surface 17 of the structure and dragged across the physical surface 17 of the structure 16. As the 3D contact scanner 12 is being dragged across the surface 17, the 3D contact scanner 12 is intermittently stopped at certain points of the plurality of points 25 on the surface 17. Each time the 3D contact scanner 12 is stopped, the depth gauge 418 is able to measure the depth of at least one point of the plurality of points 25 to help determine damage or at least changes to the topography of the surface 17. This process, e.g., dragging and stopping of the 3D contact scanner 12 having the depth gauge 418, is repeated until the depth of a sufficient amount of points of the plurality of points 25 are measured and a topographical map of the surface 17 of the structure 16, for example, is able to be built. In one example, one or more of the data collection modules 38, 48 and the data analysis modules 39, 49 of the 3D contact scanner and the data analysis system 20 of the property inspection system 10, respectively, generate the topographical map of the surface 17.

Figure 7:
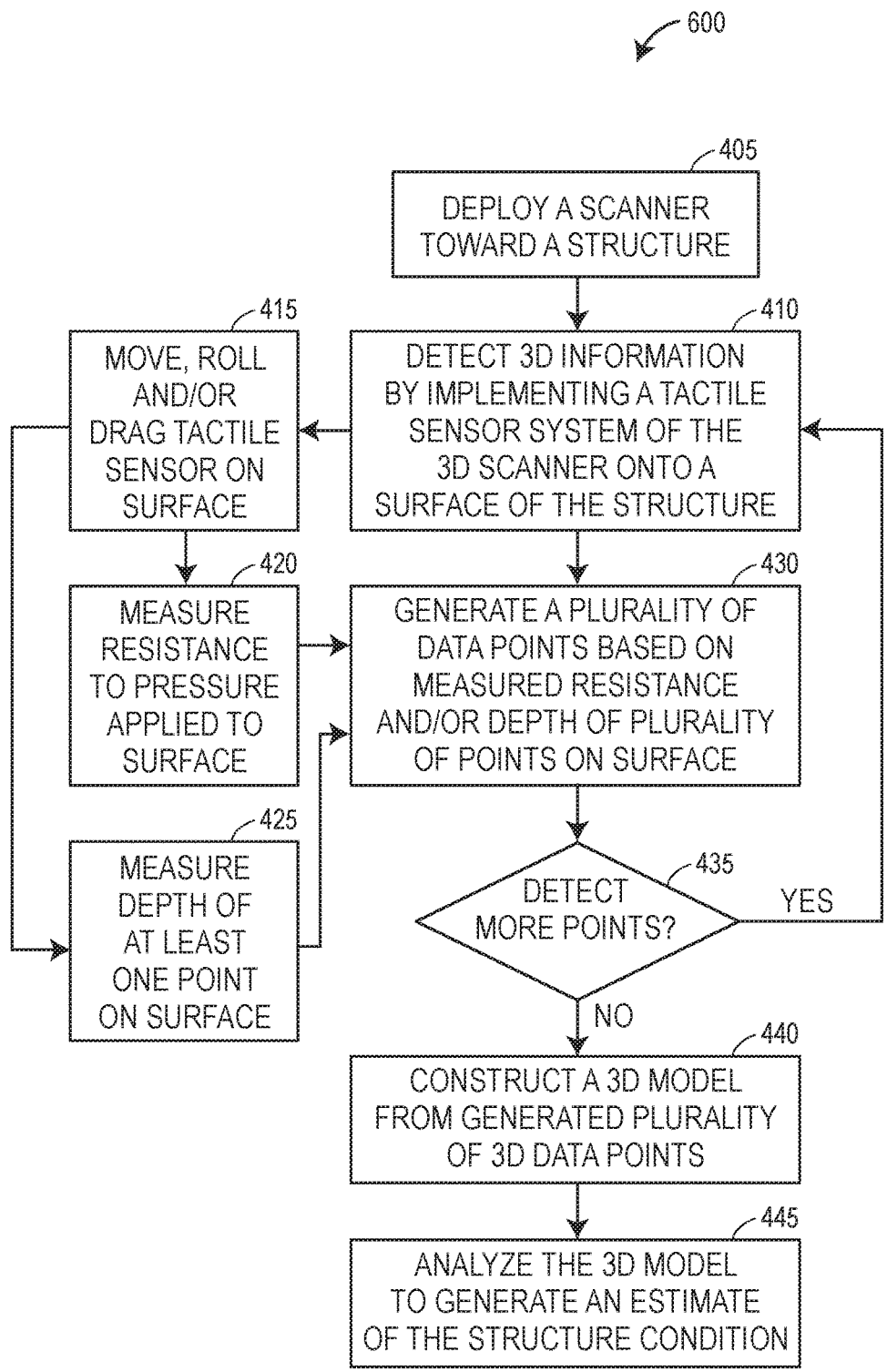
FIG. 7 is an exemplary flow chart depicting a method of one aspect of the present disclosure.

Referring now to FIG. 7, a flow chart of an example method 600 for inspecting and analyzing the condition of a structure is depicted. The method 600 may be implemented, in whole or in part, on one or more devices or systems such as those shown in the property inspection system 10 of FIGS. 1 and 2, the tactile sensor system 18 of FIG. 3, the 3D contact scanner 112 of FIG. 4A, the scanner 212 of FIG. 5A, or the scanner 312 of FIG. 6A. The method may be saved as a set of instructions, routines, programs, or modules on memory such as memory 34 of FIG. 2, and may be executed by a processor such as processor 32 of FIG. 2.

The method 600 begins when a 3D contact scanner 12, 112, 212, 312, is deployed toward and onto a structure (block 405), such as the structure 16 shown in FIG. 1. After deployment, the 3D contact scanner 12, 112, 212, 312 detects 3D information by implementing a tactile sensor system 18, 118, 218, 318 of the 3D contact scanner 12, 112, 212, 312, onto the surface 17 of the structure (block 410). Said another way, the 3D contact scanner 12, 112, 212, 312 at block 410 detects a point of the plurality of points 25 (FIG. 1), for example, on the surface 17 of the structure by having the tactile sensor system 18, 118, 218, 318 physically contact the surface 17 of the structure. As noted, the structure may be any kind of building or structure, such as a single-family home, townhome, condominium, apartment, storefront, or retail space, and the structure may be owned, leased, possessed, or occupied by an insurance policy holder. The structure may also be any of the structure types discussed regarding FIG. 1, such as a vehicle, boat, or aircraft. In such structures, the 3D contact scanner may be used to inspect the body panels, windows, frame, and other surfaces associated with the vehicle, boat, or aircraft.

In block 415, the 3D contact scanner 12, 112, 212, 312 with the tactile sensor system 18, 118, 218, 318 is one or more of moved, rolled or dragged onto the physical surface 17 of the structure, such that at least one tactile sensor 30, 130, 230, 330 of the tactile sensor system 18, 118, 218, 318 is moved, rolled or dragged on or onto the physical surface 17 of at the structure 16. In block 420, the at least one tactile sensor 30, such as the pinscreen stamp 118 and/or the roller device 218 measure resistance to pressure being applied toward the surface 17. The 3D contact scanner 12, 112, 212, 312 then generates a plurality of 3D data points based on the measured resistance at block 430. In addition or alternatively, after block 415, the depth of at least one point of the plurality of points 25 on the surface 17 of the structure 16 is measured. The 3D contact scanner 12, 112, 212, 312 then again generates a plurality of 3D data points based on the measured resistance at block 430. At least one processor, such as the processor 32 of the 3D contact scanner 12, 112, 212, 312 determines whether enough points of the plurality of points 25 on the surface 17 of the structure 16 have been detected or whether more points need to be detected (block 435). If enough points have been detected, a processor 32 of the 3D contact scanner 12, 112, 212, 312 constructs a 3D model from the generated plurality of 3D data points (block 440). Next the processor 32 of the 3D contact scanner 12, 112, 212, 312, for example, may analyze the 3D model to identify one or more features associated with the structure 17 and generate an estimate of the structure condition (block 445). In addition or alternatively, the data analysis module 39 of the 3D contact scanner 12, 112, 212, 312 or the data analysis module 49 of the data analysis system 20 may also analyze the 3D model to identify the one or more features associated with the structure 17 (block 445).

If, however, at block 435, it is determined that more points need to be detected, the 3D contact scanner 12, 112, 212, 312 detects more 3D information by implementing the tactile sensor system 18, 118, 218, 318 of the 3D contact scanner 12, 112, 212, 312 again onto the surface 17 of the structure 16 (block 410). Then once again, the 3D contact scanner 12, 112, 212, 312 with the tactile sensor system 18, 118, 218, 318 is one or more of moved, rolled or dragged onto the physical surface 17 of the structure, such that at least one tactile sensor 30, 130, 230, 330 of the tactile sensor system 18, 118, 218, 318 is moved, rolled or dragged on or onto the physical surface 17 of at the structure 16 (block 415). The process of blocks 415, 420 and/or 425 and 430 described above continue until it is determined at block 435 that enough points have been detected. The process of blocks 440 and 445, as described above, then continue to ultimately generate an estimate of the condition of the structure 16 based on the plurality of 3D data points generated by the 3D contact scanner 12, 112, 212, 312.

In one example operation of the tactile sensor 30, 130, 230, 330 of the 3D contact scanner 12, 112, 212, 312, the tactile sensor 30, 130, 230, 330 receives a signal from the 3D contact scanner 12, 112, 212, 312 instructing the tactile sensor 30, 130, 230, 330 to detect topographical features associated with a surface ("tactile capture signal"). The tactile sensor 30, 130, 230, 330 receives the tactile capture signal and the tactile sensor 30, 130, 230, 330 is exposed to a surface associated with the structure 16. The tactile sensor 30, 130, 230, 330 generates tactile data representing at least some of the shapes and features of the surface that the tactile sensor 30, 130, 230, 330 was exposed to. The 3D contact scanner 12, 112, 212, 312 then uses the tactile data to generate 3D data. Alternatively, the tactile sensor 30, 130, 230, 330 may transmit the tactile data to the memory 34, 44 where the tactile data is stored.

In alternative examples of the property inspection system 10, the tactile capture signal may be received from the processor 32 (FIG. 2) of the 3D contact scanner 12, for example, wherein the respective signal was generated in response to a capture command received by the processor 32 from the network interface 36, or the input interface 31. Likewise, the processor 32 may also operate to transmit the tactile data, or 3D data, to the network interface 36 to be transmitted to another device or system.

In operation of the property inspection system 10, the 3D contact scanner 12, 112, 212, 312 is deployed on a surface associated with the structure 16. The 3D contact scanner 12, 112, 212, 312 comes into contact with the surface and moves, e.g., rolls, drags, pulls. At least one tactile sensor 30, 130, 230, 330 internal or external to the 3D contact scanner 12, 112, 212, 312 detects the imprinted texture. The 3D contact scanner 12, 112, 212, 312 generates tactile data representing the imprinted texture uses the tactile data to generate 3D data. In another example, the antenna 15, 115, 215, 315 of the 3D contact scanner 12, 112, 212, 312 may transmit the 3D data to the antenna 23 of the base station 20 (FIG. 2).

In addition, the network interface 36 (FIG. 2) receives 3D data points corresponding to a structure such as the structure 16 shown in FIG. 1. The network interface 36 transmits the received data to the memory 34. The processor 32 accesses the memory 34 to generate a first 3D model of the structure based on the 3D data points, wherein the edges and vertices associated with the model are derived from the 3D data points. The processor 32 may then make one or more comparisons between the first 3D model and one or more second models. The second models may represent previously received data relating to the same structure, or they may represent previously received data relating to similar structures. Alternatively, the second models may have been created specifically for the purpose of estimating the condition of a structure and may not relate to any actual physical structure. Based on the one or more comparisons, the processor 32 generates an estimate of the condition of the structure. The estimate of the condition of the structure is saved to the memory 34. In some embodiments, network interface 36 may receive 2D image data or 2D-3D combination image data and may transmit the data to the memory 34. The processor 32 may identify features with the 2D images and/or 2D-3D combination images and may generate the estimate of the condition of the structure in accordance with the identified features.

In further operation of the property inspection system 10, the processor 32 may determine, based on the generated estimate, that the structure 16 has been damaged. The processor 32 may then operate to calculate (based on the condition of the structure and data relating to costs such as cost of supplies, materials, components and labor) an estimated financial cost associated with the damage. The estimated financial cost is then saved to the memory 34. A video interface (not shown) may be used to display: the first 3D model, any of the one or more second models, the estimate of the condition of the structure, or the estimated financial cost.

In alternative embodiments of the property inspection system 10, the received data may also represent topographical maps, which may be displayed via the video interface (not shown). The received data may then be used to generate a 3D model. Alternatively, the received data may be compared to reference topographical maps to estimate the condition of the structure.

Overall, one of ordinary skill in the art will appreciate the various advantages of the property inspection system 10 of the present disclosure. For example, the property inspection system 10 of the present disclosure is able to accurately detect 3D information about the surface of the structure using at least one tactile sensor 30, 130, 230, 330. By physically contacting the surface of the damaged structure, the at least one tactile sensor 30, 130, 230, 330 is able to provide more accurate information about the surface, unlike 2D and 3D scanning methods involving ultrasonic scanning or radar detection, for example. Unlike those 2D and 3D scanning methods that do not require physical contact between a 3D contact scanner and the surface of the structure, the present invention requires such physical contact, and, therefore, any sunlight or lack thereof does not affect the accuracy of the information detected by the tactile sensors 30, 130, 230, 330, for example. As a result, significantly more accurate 3D information about the surface of the structure is able to be detected by at least one tactile sensor 18, 118, 218, 318, ultimately resulting in a more accurate estimate or appraisal of the structure by the property inspection system 10.

Still further, the present disclosure also does not require any jelly-like conductor or any other substrate be first applied to the surface of the structure in order to detect 3D information about the structure. Because such a substrate is not required, there is, of course, no further requirement to remove such a substrate after 3D scanning or detection. This ultimately makes the process and system 10 of the present disclosure less messy and costly than other 2D and 3D scanning methods using such substrates or jelly-like sound conductors to get information about the structure surface.

The following additional considerations apply to the foregoing discussion. Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Discussions herein referring to an "appraiser," "inspector," "adjuster," "claim representative" or the like are non-limiting. One skilled in the art will appreciate that any user associated with an insurance company or an insurance function may utilize one or more of the devices, systems, and methods disclosed in the foregoing description. One skilled in the art will further realize that any reference to a specific job title or role does not limit the disclosed devices, systems, or methods, or the type of user of said devices, systems, or methods.

Certain implementations are described herein as including logic or a number of components, modules, or mechanisms. Modules may constitute either software modules (e.g., code implemented on a tangible, non-transitory machine-readable medium such as RAM, ROM, flash memory of a computer, hard disk drive, optical disk drive, tape drive, etc.) or hardware modules (e.g., an integrated circuit, an application-specific integrated circuit (ASIC), a field programmable logic array (FPLA)/field-programmable gate array (FPGA), etc.). A hardware module is a tangible unit capable of performing certain operations and may be configured or arranged in a certain manner. In example implementations, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one implementation," "one embodiment," "an implementation," or "an embodiment" means that a particular element, feature, structure, or characteristic described in connection with the implementation is included in at least one implementation. The appearances of the phrase "in one implementation" or "in one embodiment" in various places in the specification are not necessarily all referring to the same implementation.

Some implementations may be described using the expression "coupled" along with its derivatives. For example, some implementations may be described using the term "coupled" to indicate that two or more elements are in direct physical or electrical contact. The term "coupled," however, may also mean that two or more elements are not in direct contact with each other, but yet still co-operate or interact with each other. The implementations are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the implementations herein. This is done merely for convenience and to give a general sense of the invention. This description should be read to include one or at least one and the singular also includes the plural unless it is obvious that it is meant otherwise.

Upon reading this disclosure, those of skill in the art will appreciate still additional alternative structural and functional designs for a system and a process for inspecting a structure to estimate the condition of a structure through the disclosed principles herein. Thus, while particular implementations and applications have been illustrated and described, it is to be understood that the disclosed implementations are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

We claim:

1. A property inspection system for determining the condition of a physical structure, the property inspection system comprising:
   one or more 3D contact scanners adapted to scan a surface of a structure;
   at least one tactile sensor system coupled to the one or more 3D contact scanners, the tactile sensor system including at least one tactile sensor having a pinscreen stamp; and
   one or more processors for generating 3D data points corresponding to the 3D information detected by the tactile sensor system.

2. The system of claim 1, the pinscreen stamp having a plurality of pins adapted to form an imprint of a plurality of points on the surface of the structure when pressure is applied to the pinscreen stamp in the direction of the surface of the structure.

3. A property inspection system for determining the condition of a physical structure, the property inspection system comprising:
   one or more 3D contact scanners adapted to scan a surface of a structure;
   at least one tactile sensor system coupled to the one or more 3D contact scanners, the tactile sensor system including at least one tactile sensor having a roller device having a plurality of disks; and
   one or more processors for generating 3D data points corresponding to the 3D information detected by the tactile sensor system.

4. The system of claim 3, wherein the at least one tactile sensor comprises the roller device, the roller device including a plurality of disks adapted to contact the physical surface of the structure, such that when zero pressure is applied to at least one disk of the plurality of disks in the direction of the surface of the structure, the height of the at least one disk of the plurality of disks is measured from a top surface of the structure to define a threshold, and when a first pressure is applied to the at least one disk of the plurality of disks in the direction of the surface of the structure, the height of the at least one disk of the plurality of disks is measured from the top surface of the structure and compared to the threshold.

5. A property inspection system for determining the condition of a physical structure, the property inspection system comprising:
   one or more 3D contact scanners adapted to scan a surface of a structure;

at least one tactile sensor system coupled to the one or more 3D contact scanners, the tactile sensor system including at least one tactile sensor having a whisker device; and one or more processors for generating 3D data points corresponding to the 3D information detected by the tactile sensor system.

6. The system of claim 5, the at least one whisker of the whisker device comprising a whisker having a pivot point, such that one or more of an angle of deflection or an angle of rotation of the at least one whisker from an axis of the pivot point is detected to measure a depth of at least one point of the plurality of points on the surface of at least part of the structure.

7. The system of claim 5, the whisker device comprising a piezoelectric sensor, such that a voltage generated, if any, by the piezoelectric sensor at least one point of the plurality of points on the surface of the structure is measured to determine a depth of at least one point of the plurality of points.

\* \* \* \* \*